US011185682B2

(12) United States Patent
Farnan

(10) Patent No.: US 11,185,682 B2
(45) Date of Patent: Nov. 30, 2021

(54) BLOOD PUMP WITH RESTART LOCKOUT

(71) Applicant: HeartWare, Inc., Miami Lakes, FL (US)

(72) Inventor: Robert C. Farnan, Fort Lauderdale, FL (US)

(73) Assignee: HeartWare, Inc., Miami Lakes, FL (US)

(*) Notice: Subject to any disclaimer, the term of this patent is extended or adjusted under 35 U.S.C. 154(b) by 226 days.

(21) Appl. No.: 16/547,046

(22) Filed: Aug. 21, 2019

(65) Prior Publication Data
US 2019/0374694 A1 Dec. 12, 2019

Related U.S. Application Data

(62) Division of application No. 15/377,671, filed on Dec. 13, 2016, now Pat. No. 10,426,879.
(Continued)

(51) Int. Cl.
| | |
|---|---|
| *A61M 1/10* | (2006.01) |
| *A61M 60/50* | (2021.01) |
| *G16H 40/63* | (2018.01) |
| *A61M 60/422* | (2021.01) |
| *A61M 60/871* | (2021.01) |

(52) U.S. Cl.
CPC .......... *A61M 60/50* (2021.01); *A61M 60/422* (2021.01); *A61M 60/871* (2021.01); *G16H 40/63* (2018.01)

(58) Field of Classification Search
CPC .... A61M 1/101; A61M 1/122; A61M 1/1086; A61M 2205/3334
See application file for complete search history.

(56) References Cited

U.S. PATENT DOCUMENTS 5,711,753 A * 1/1998 Pacella ............... A61M 60/205
                                                    600/16
6,183,412 B1 * 2/2001 Benkowski ......... A61M 60/422
                                                    600/16
(Continued)

OTHER PUBLICATIONS

International Search Report and Written Opinion dated Mar. 8, 2017, for corresponding International Application No. PCT/US2016; International Filing Date: Dec. 13, 2016 consisting of 9 pages.

*Primary Examiner* — Michael J D'Abreu
(74) *Attorney, Agent, or Firm* — Christopher & Weisberg, P.A.

(57) ABSTRACT

A control circuit includes a pump shutdown module responsive to one or more inputs indicating at least from the group consisting of an operational error at the implantable blood pump and an adverse physiological state of a user of the implantable blood pump. The pump shutdown module ceases operation of the implantable blood pump in response to the one or more inputs. A pump restart module configured to resume operation of the implantable blood pump in response to a first pump restart input and a second pump restart input is included. A pump restart lockout module configured to initiate a pump lockout mode in response to a lockout input is included. The pump lockout mode prevents resumption of operation of the implantable blood pump in response to the first pump restart input and allows resumption of operation of the implantable blood pump in response to the second pump restart input.

8 Claims, 5 Drawing Sheets

Related U.S. Application Data

(60) Provisional application No. 62/266,871, filed on Dec. 14, 2015.

(56) References Cited

U.S. PATENT DOCUMENTS

| | | |
|---|---|---|
| 6,254,359 B1 | 7/2001 | Aber |
| 7,972,122 B2 | 7/2011 | LaRose et al. |
| 8,007,254 B2 | 8/2011 | LaRose et al. |
| 8,419,609 B2 | 4/2013 | Shambaugh, Jr. et al. |
| 8,512,013 B2 | 8/2013 | LaRose et al. |
| 9,427,508 B2 | 8/2016 | Reyes et al. |
| 9,492,601 B2 | 11/2016 | Casas et al. |
| 2009/0156885 A1 | 6/2009 | Morello et al. |
| 2014/0100413 A1 | 4/2014 | Casas et al. |
| 2014/0357937 A1 | 4/2014 | Reyes et al. |
| 2016/0144092 A1 | 5/2016 | Casas et al. |

\* cited by examiner

400

BLOOD PUMP WITH RESTART LOCKOUT

CROSS-REFERENCE TO RELATED APPLICATION

This application is a divisional of U.S. application Ser. No. 15/377,671, filed Dec. 13, 2016, now U.S. Pat. No. 10,426,879, issued Oct. 1, 2019, and is related to and claims priority to U.S. Provisional Patent Application Ser. No. 62/266,871, filed Dec. 14, 2015, entitled BLOOD PUMP WITH RESTART LOCKOUT, the entirety of which is incorporated herein by reference.

STATEMENT REGARDING FEDERALLY SPONSORED RESEARCH OR DEVELOPMENT n/a

TECHNICAL FIELD

The present invention relates to methods and devices for controlling and monitoring operation of an implantable blood pump.

BACKGROUND

An implantable blood pump used as a mechanical circulatory support device or "MCSD" includes a pumping mechanism to move blood. The pumping mechanism may be a radial flow pump, such as the HVAD® Pump manufactured by HeartWare, Inc. in Miami Lakes, Fla., USA. The HVAD® Pump is further discussed in U.S. Pat. No. 8,512,013, the disclosure of which is hereby incorporated herein in its entirety. Alternatively, the pumping mechanism may be an axial flow pump, such as the MVAD® Pump, also manufactured by HeartWare, Inc., and the pumps described in U.S. Pat. Nos. 7,972,122, 8,007,254 and 8,419,609, the disclosures of which are also hereby incorporated herein in their entirety, or any other pump suitable for providing vascular assistance. In operation, the blood pump draws blood from a source such as the right ventricle, left ventricle, right atrium, or left atrium of a patient's heart and propels the blood into an artery such as the patient's ascending aorta or peripheral artery. Due to the nature of the application, the pumping mechanism must be highly reliable. Patient comfort is also a significant consideration. In addition to the pumping mechanism, the device may include a controller and the drive electronics for the pumping mechanism. The controller and drive electronics may receive power from an external power source. That power may be used to drive the pumping mechanism.

The control circuit may be configured to monitor operation of the blood pump. During such monitoring, if the control circuit detects the presence of an undesirable condition at either the blood pump or the patient's heart (near the blood pump), the control circuit may take action to address the undesirable condition, e.g., provide an alert to the patient or clinician, control operation of a motor of the pump to attempt to clear the undesirable condition, etc. In some cases the patient's heart has sufficient pumping capacity to sustain life for at least a limited time. For instance, where the blood pump provides only partial support to the patient, stoppage of the pump may cause the patient to revert back to a diseased condition or state (e.g., due to degenerative heart failure), in which the patient's heart can sustain life for at least a limited time. In such cases, controlling operation of the pump may involve stopping operation of the pump until the undesirable condition clears. Operation of the pump may then be automatically restarted or manually restarted, directly or indirectly, by the patient (e.g., providing power the pump) or by a clinician.

Generally, where operation of the pump has stopped, it may be desirable to provide the pump with a way of promptly, manually restarting so that it may resume providing its intended assistance to the patient. However, under some circumstances, it may be undesirable to restart operation of the pump. For instance, if the pump is idle for a long enough time, there may an increased risk of thrombosis in the pump, such that sudden restarting of the pump may propel a clot into the blood stream of the patient. Under such circumstances, it may be necessary to initially examine and subsequently monitor the patient to ensure that restarting the pump does not pose a risk to the patient's health. It may also be desirable under such circumstances to prevent the patient or a clinician from restarting the pump without first examining or monitoring the patient, or at least without making an informed decision given the risk associated with restarting the pump after an extended cessation.

SUMMARY

The present invention advantageously provides for a control circuit for controlling operation of an implantable blood pump. The control circuit includes a pump shutdown module responsive to one or more inputs indicating at least from the group consisting of an operational error at the implantable blood pump and an adverse physiological state of a user of the implantable blood pump. The pump shutdown module is further configured to cease operation of the implantable blood pump in response to the one or more inputs. A pump restart module configured to resume operation of the implantable blood pump in response to a first pump restart input and a second pump restart input is included. A pump restart lockout module configured to initiate a pump lockout mode in response to a lockout input is included. The pump lockout mode prevents resumption of operation of the implantable blood pump in response to the first pump restart input and allows resumption of operation of the implantable blood pump in response to the second pump restart input.

In another aspect of this embodiment, the first pump restart input is an automatic input provided to the control circuit, and the second pump restart input is a manual input provided to the control circuit.

In another aspect of this embodiment, the second pump restart input is inaccessible to the user of the implantable blood pump.

In another aspect of this embodiment, the second pump restart input includes an instruction to clear the pump lockout mode.

In another aspect of this embodiment, the lockout input indicates that an amount of time since ceasing operation of the implantable blood pump exceeds a predetermined amount of time.

In another aspect of this embodiment, the predetermined amount of time is based on a determined risk of thrombosis in the implantable blood pump occurring after the predetermined amount of time.

In another aspect of this embodiment, the instruction to reset the pump lockout mode includes resetting the determined risk of thrombosis in response to the second pump restart input.

In another aspect of this embodiment, an alert module is configured to notify the user of initiation of the pump lockout mode.

In another aspect of this embodiment, the one or more inputs includes at least one from the group consisting of a low flow condition, low power condition, suction condition, high pressure condition, and overheating condition.

In another aspect of this embodiment, the first pump restart input includes at least one from the group consisting of clearance of high pressure condition, clearance of suction condition, clearance of low flow condition, and clearance of overheating condition.

In another aspect of this embodiment, the second pump restart input includes manual entry of the first pump restart input and an instruction to clear the lockout mode.

In another embodiment, a method for controlling operation of an implantable blood pump having a motor includes ceasing operation of the motor. A control circuit receives one from the group consisting of a first pump restart input and a second pump restart input configured to resume operation of the motor. The control circuit determines whether the control circuit has initiated a pump lockout mode in response to a lockout input. In response to a determination that the pump lockout mode has not been initiated, operation of the motor is resumed in response to one from the group consisting of the first pump restart input and the second pump restart input. In response to a determination that the pump lockout mode has been initiated, operation of the motor in response to the second pump restart input is resumed and operation of the motor in response to the first pump restart input is maintained ceased.

In another aspect of this embodiment, the second pump restart input is a manual input.

In another aspect of this embodiment, the second restart pump input is inaccessible to a user of the implantable blood pump.

In another aspect of this embodiment, in response to a determination that the pump lockout mode has been initiated, clearing the pump lockout mode in response to the second pump restart input.

In another aspect of this embodiment, the pump lockout mode is initiated at a predetermined amount of time after ceasing operation of the motor.

In another aspect of this embodiment, the predetermined amount of time is based on a predicted risk of thrombosis in the implantable blood pump.

In another aspect of this embodiment, the second pump restart input resets the predetermined amount of time.

In another aspect of this embodiment, at least one of a user and a clinician is notified of the implantable blood pump initiation of the pump lockout mode.

In yet another embodiment, an implantable blood pump control system includes an implantable blood pump having a motor. A control circuit in communication with the motor is included, the control circuit includes a pump control module configured to control operation of the motor when the motor is operating. The control circuit further includes a pump shutdown module responsive to one or more inputs indicating at least from the group consisting of an operational error at the implantable blood pump and an adverse physiological state of a user of the implantable blood pump. The pump shutdown module being further configured to cease operation of the implantable blood pump in response to the one or more inputs. The control circuit further includes a first pump restart module configured to resume operation of the implantable blood pump in response to a first pump restart input. The first pump restart input is automatic input. The first pump restart module being further configured to resume operation of the implantable blood pump in response a second pump restart input. The second pump restart input is a manual input inaccessible to a user of the implantable blood pump. The control circuit further includes a pump restart lockout module configured to initiate a pump lockout mode in response to a lockout input. The lockout input indicates that an amount of time since ceasing operation of the implantable blood pump exceeds a predetermined amount of time based on a determined risk of thrombosis in the implantable blood pump occurring after the predetermined amount of time. The pump lockout mode prevents resumption of operation of the implantable blood pump in response to the first pump restart input and allows resumption of operation of the implantable blood pump in response to the second pump restart input.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The present disclosure provides control devices, systems and methods that facilitate restarting operation of a blood pump in some, wanted circumstances, while preventing restarting the pump in other, unwanted circumstances. The devices, systems and methods of the present disclosure desirably are also capable of determining when it is desirable to allow or prevent restarting of the pump.

Figure 1:
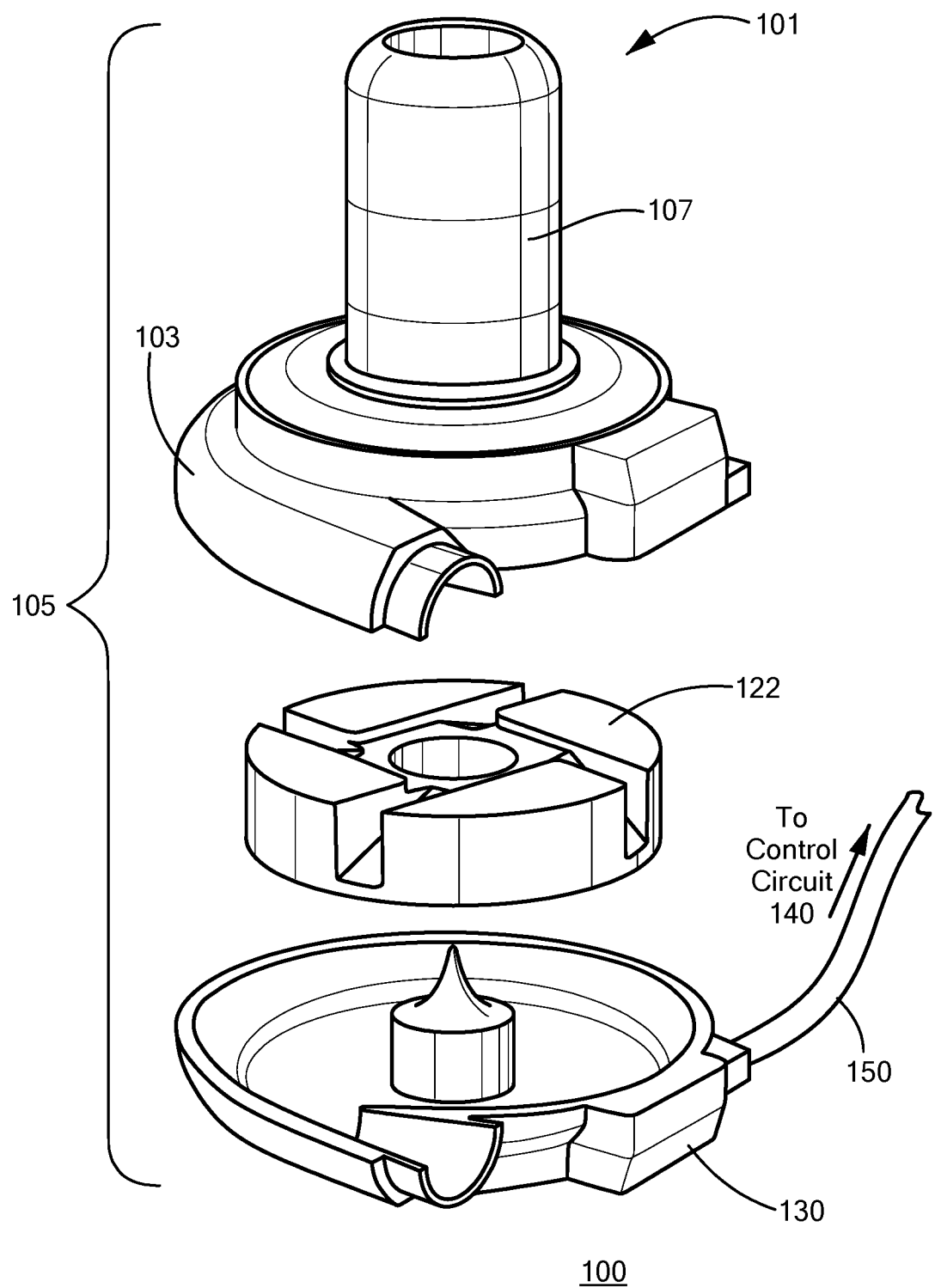
FIG. 1 is an exploded perspective view of a blood pump system in accordance with an aspect of the disclosure.

Now referring to the drawings in which like reference designators refer to like elements, there is shown in FIG. 1 an exemplary a blood pump system 100 constructed in accordance with one embodiment of the invention. The blood pump system 100 according to this embodiment includes a control circuit 140 connected via a cable feed 150 to a centrifugal blood pump 101. In one configuration, the control circuit 140 is disposed within a sterile housing (not shown) remote from the blood pump 101 and within the body of the patient. In other configurations, the control circuit 140 is external to the patient, for example, coupled within a battery pack (not shown) and in communication with the blood pump 101 through, for example, wireless, Bluetooth, or NFC. The blood pump 101 includes a housing 105 including interlocking casings forming a closed pumping chamber 103 between them. Blood is supplied to the pump 101 through an axial inlet cannula 107 adapted for apical insertion into a heart ventricle, for example, the left ventricle. The cannula 107 is affixed to or may be integral with the housing 105 and is in fluid flow communication with the pumping chamber 103. Blood exits the pumping chamber 103 through an outlet 113 opposite the inlet cannula 107 in a direction substantially perpendicular to the longitudinal axis of the inlet cannula 107.

A motor rotor or pump impeller 122 is disposed within the pumping chamber 103. In operation, blood entering the cannula 107 from a heart ventricle passes into the pumping chamber 103 where it is engaged by the rotating impeller 122. Blood entering the pumping chamber from the cannula 107 is redirected from axial flow exiting the cannula to a radial flow within which the impeller 122 is submerged. The housing 105 may contain an electrical feed through connector 130 for a power and control cable to supply power to the motor 122. The cable feed 150 carrying a plurality of cables is connected to the pump through the connector 130. The cables in the feed 150 may carry electrical power and control instructions to the pump 101.

Figure 2:
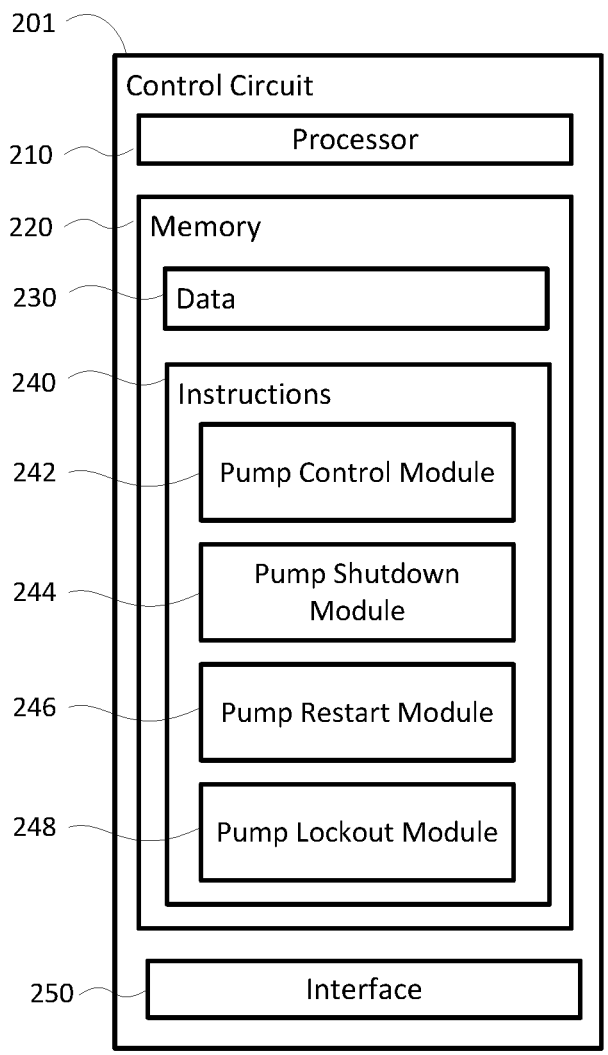
FIG. 2 is a block diagram of an example control circuit for the implantable blood pump shown in FIG. 1.

Referring now to FIG. 2, control circuit 201, which is an exemplary control circuit 140, is in communication with the pump 101 and monitors and further controls operation of the pump 101. The functions of control circuit 201 may be implemented at least in part by a general-purpose processor 210, a memory 220 and an interface 250. Memory 220 stores information accessible by processor 210, including instructions 240 that may be executed by the processor 210. The memory 220 also includes data 230 that may be retrieved, manipulated or stored by the processor 210. The memory may be of any type capable of storing information accessible by the processor, such as a hard-drive, memory card, ROM, RAM, DVD, CD-ROM, write capable, and read-only memories. The processor 210 may be any well-known processor, such as commercially available processors. Alternatively, the processor may be a dedicated controller such as an ASIC.

Data 230 may be retrieved, stored or modified by processor 210 in accordance with the instructions 240. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data. Although FIG. 2 functionally illustrates the processor and memory as being within the same block, it will be understood that the processor and memory may actually comprise multiple processors and memories that may or may not be stored within the same physical housing. The memory may include one or more media on which information can be stored. In one configuration, the medium holding the instructions retains the instructions in non-transitory form. Some or all of the instructions and data may be stored in a location physically remote from, yet still accessible by, the processor. Similarly, the processor may comprise a collection of processors which may or may not operate in parallel. The control circuit 201 described above may be operated using the methods described herein. It should be understood that some operations may be performed separately from other operations. Moreover, operations may be added or omitted.

Continuing to refer to FIG. 2, the control circuit 201 includes hardware and software for controlling the various aspects of the operation of the pump 101. The instructions 240 stored in the memory 220 may include one or more instruction sets or modules for performing certain operations. One such module may be a pump control module 242 for controlling operation of the motor while the pump is running (e.g., increasing or decreasing pump speed), such as in response to determination of the presence or absence of a suction condition in the pump.

Another such module may be a pump shutdown module 244 for ceasing operation of the motor of the pump in response to one or more inputs. The one or more inputs may be indicative of an undesirable condition, such as an operational error at the pump or at electronics (or a battery) associated with the pump 101, or an adverse physiological state of the patient (e.g., low flow condition, suction condition, high pressure condition, overheating of internal electronics, or other conditions as described in commonly owned and copending U.S. Application Ser. Nos. 13/951,302, 14/294,448, and 14/950,213, the disclosures of which are hereby incorporated by reference herein in its entirety).

The instructions 240 may further include a pump restart module 246 for resuming or restarting operation of the pump 101 and its motor 122, after operation has been ceased, in response to a restart input. In some examples, the restart input may be automatically generated by the control circuit 201. For instance, if the undesirable condition that prompted ceasing operation was an overheating of the control circuit 201 or a power supply, the control circuit 201 may automatically resume operating the pump 101 and its motor 122 after the temperature of an overheated component drops to a tolerable temperature. For further instance, if the undesirable condition was a power shortage or depletion, the control circuit 201 may automatically resume operation of the pump 101 and its motor 122 when it is provided sufficient power to operate (e.g., is plugged in to a power source). In other examples the restart input may be manually provided by a patient using the pump 101, or by a doctor or clinician of the patient.

The instructions 240 may further include a pump lockout module 248 for initiating a mode of operation (hereinafter referred to as a lockout mode) in which the pump 101 and its motor 122 cannot be restarted based on one or more restart inputs. The lockout mode may be initiated under conditions in which it may be undesirable to abruptly restart the motor 122, for instance where the pump 101 has been stopped for a duration of time that may increase the risk of thrombosis (clotting) at the pump 101. The lockout mode may be initiated based on a lockout input, which may indicate the amount of time since operation of the pump 101 has ceased exceeding a preset value or predetermined amount of time.

The lockout mode may eventually be cleared by a different input, referred to as a lockout clearance input, at which point the operation of the pump may be resumed using the pump restart module 246. The lockout clearance input may a restart input, since the result of clearing the lockout mode may be the resumption of operation of the pump 101. Given the aforementioned risks involved with clearing a lockout mode after its initiation, in one configuration, the lockout clearance input may be accessible only to a doctor, clinician, or other person capable of examining and monitoring the patient for health risks when the pump is restarted.

The control circuit 201 may further include an interface 250 for communicatively connecting the control circuit 201 to one or more other input devices. Inputs, such as data indicating an undesirable condition, or the manual inputs described herein (e.g., restart inputs, lockout clearance inputs, etc.) may be provided to the control circuit 201 via the interface 250. The interface 250 may also provide for outputting of signals, such that the control circuit 201 may alert a patient or clinician when an undesirable condition arises, and/or when the pump 101 ceases operation or initiates lockout mode. The interface 250 may be an analog interface (e.g., audio interface) or a digital interface, such as Bluetooth. TCP/IP, wi-fi, and others. Where the control circuit 201 is implemented in an implantable structure adapted to be disposed within the body of the patient, the interface 250 may include known elements for communicating signals through the skin of the patient.

Figure 3:
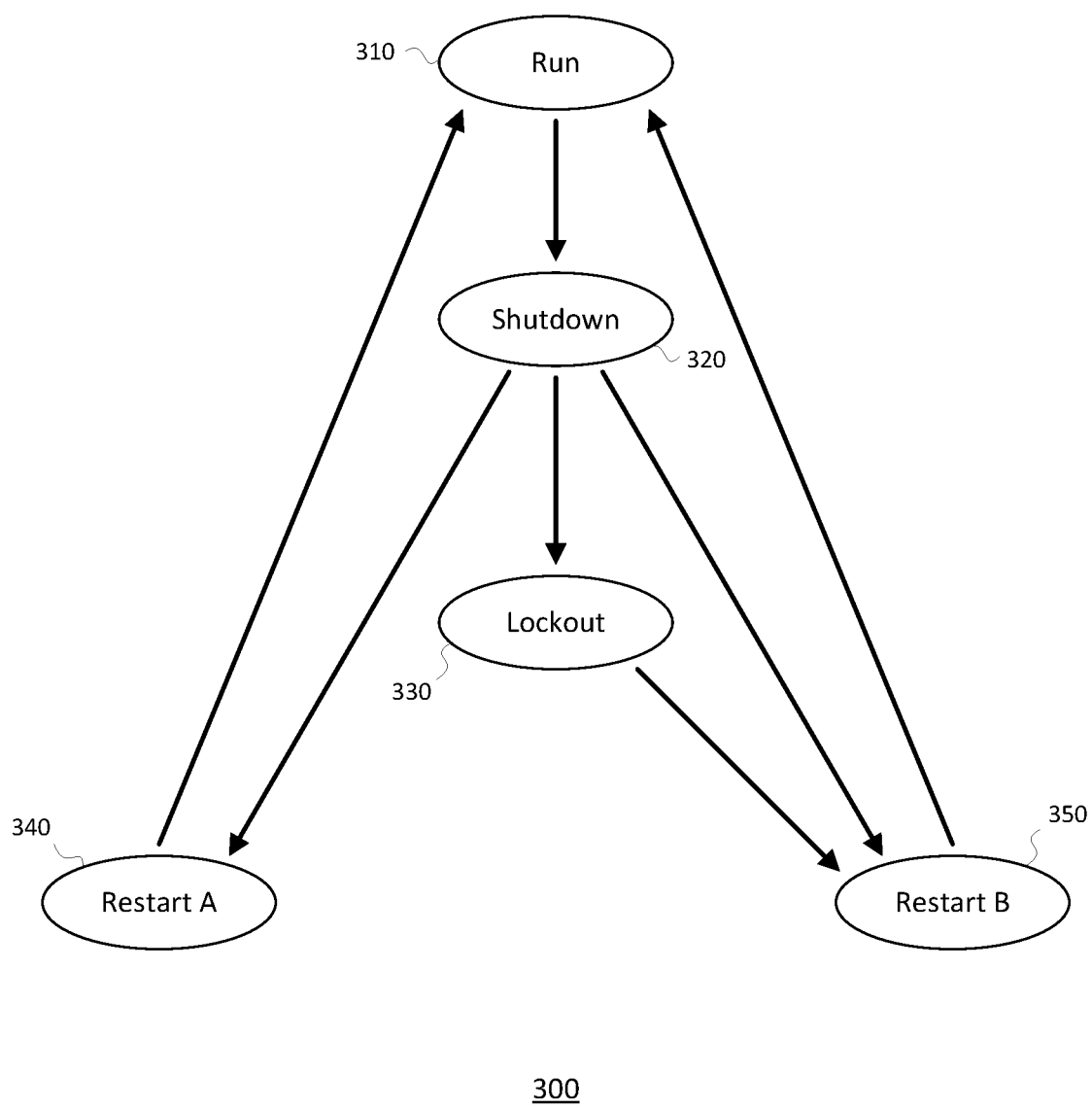
FIG. 3 is a state diagram depicting operation of a control circuit shown in FIG. 2.

Referring now to FIG. 3, the control circuit 201 may transition between various operational states in accordance with the state diagram 300 of FIG. 3. Operation of the pump 101 and its motor 122 may begin in a run state 310, in which the pump 101 is operating normally. Operation may then transition to a shutdown state 320 in which some undesirable condition causes operation of the run state 310 to cease. In the example of FIG. 3, two restart states 340 and 350 are provided for restarting operation of the pump 101 from the shutdown state 320. The first restart state ("Restart A") 340 may be transitioned to in response to one or more particular first pump restart inputs, such as those inputs that may indicate clearance of an undesirable condition (e.g., cooldown to acceptable temperature, power available etc.), or otherwise accessible to a patient or a clinician. The second restart state ("Restart B") 350 may be transitioned to in response to one or more second pump restart inputs that may be not be automated by the control circuit 201, and/or may not be as readily accessible to the patient or the clinician.

In the example of FIG. 3, both the first restart states 340 and 350 transition back to the run state 310, thereby resuming normal operation of the pump 101. In other configurations, the control circuit 201 may operate the same whether in first or second restart states 340 and 350. However, restart operations may differ depending on the particular condition that prompted the shutdown in the first place. For instance, where the pump 101 is stopped on account of an overheated or suction condition, startup may be performed at a lower speed than compared to startup after a loss of power. For further instance, restarting in some cases may involve the control circuit 201 providing an alert to the patient and/or a clinician indicating restarting the pump, whereas in other cases may not involve the control circuit 201 performing such a function.

If one or more criteria are met, for example, the pump 101 remaining in the shutdown state 320 for a threshold amount of time without transitioning to one of the first or second restart states 340, 350, then a pump restart lockout module 248 of the control circuit 201 may further transition the pump 101 to lockout state 330. The lockout state 330 may differ from the shutdown state 320 in that the control circuit 201 is prevented from transitioning to the first restart state 340 from the lockout state, that is, the control circuit 201 is prevented from responding to one of the first pump restart input and then prompting a transition to the first restart state.

As explained above, it may be beneficial to enable the control circuit 201, patient or clinician to easily and readily initiate the first restart state 340 from shutdown state 320, while at other times preventing initiation of the first restart state 340 from lockout state 330. Access to initiating the second restart state may be limited to those situations in which the patient has been examined and monitored when the pump 101 is restarted, or at least that an informed decision has been made to restart the pump 101 in view of the risks therewith.

Figure 4:
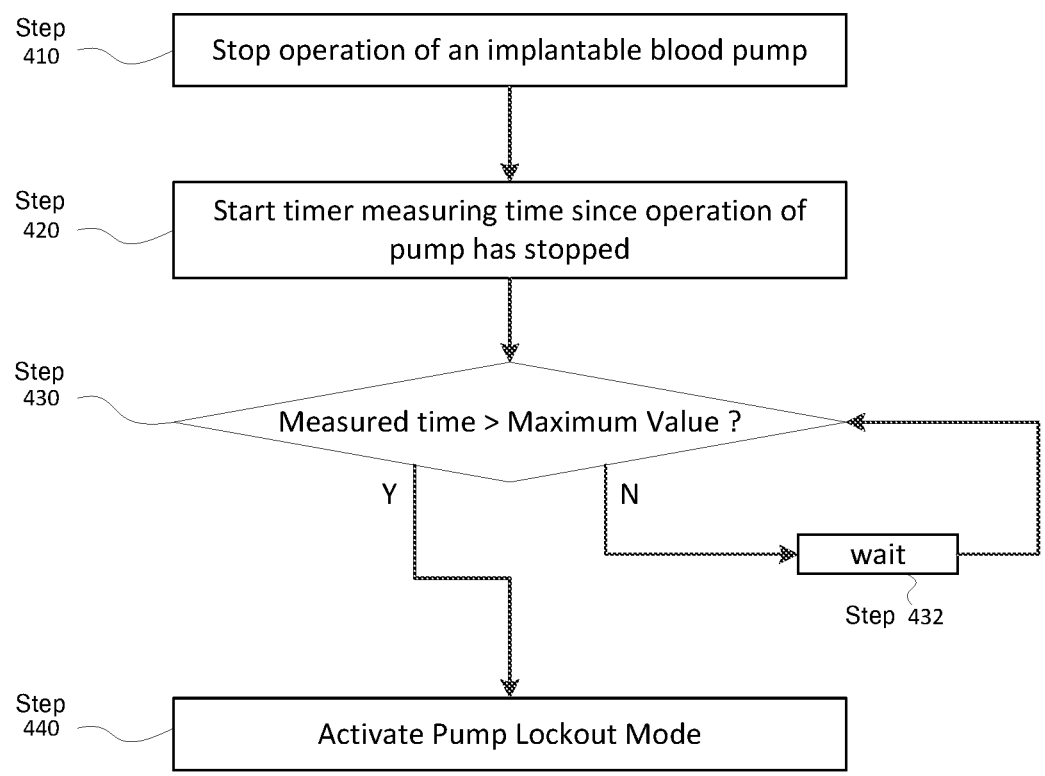
FIG. 4 is a flow diagram of a method for controlling operation of an implantable blood pump shown in FIG. 1.

Referring now to FIG. 4 in which the illustrated flow diagram provides an example routine 400 of the control circuit 201 to determine whether to activate lockout state 330 for pump 101. At Step 410, operation of the implantable blood pump 101 stops, e.g., due to a detected undesirable condition which initiates one or more inputs that may include an operational error at the implantable blood pump 101 and/or an adverse physiological state of a user of the implantable blood pump 101. At Step 420, the control circuit 201 starts a timer to measure the amount of time for which operation of the pump 101 has stopped. In some cases, stoppage of the pump 101 may be characterized as the time when the control circuit 201 received the one or more inputs indicative of an undesirable operating condition. In other cases, stoppage of the pump 101 may be characterized as the time when the pump shutdown module 244 of control circuit 201 instructs the pump 101 and its associated motor 122 to cease operation. At Step 430, the control circuit 201 compares the measured passage of time against a predetermined maximum value which may be a predetermined amount of time based on an increased risk of thrombosis. If the measured amount time does not exceed the predetermined amount of time then the control circuit 201 may wait a predetermined amount of time (at Step 432) and then repeat the comparison of Step 430. If the measured time exceeds the predetermined amount of time, then the pump restart lockout module 248 of control circuit 201 initiates activation of the lockout mode for the pump 101.

Figure 5:
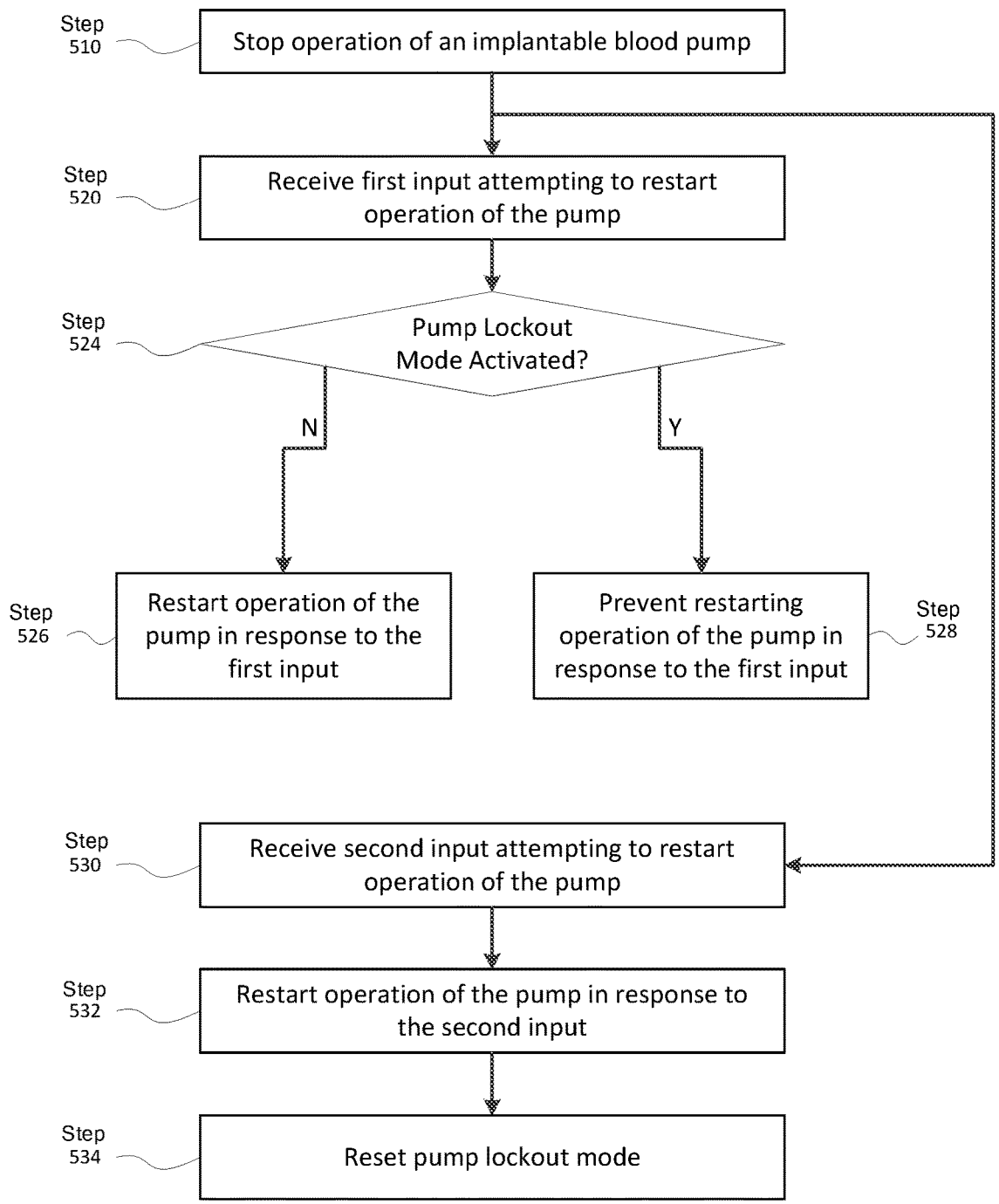
FIG. 5 is another flow diagram of a method for controlling operation of an implantable blood pump shown in FIG. 1.

Referring now to FIG. 5 in which the illustrated flow diagram provides an example routine 500 of restarting a stopped pump 101 using a control circuit 201 having multiple restart modes. In the example of FIG. 5, the control circuit 201 is given access to only one restart mode. It should be understood that the operations of the routine 500 do not have to be performed in the precise order described below. Rather, various operations can be handled in a different order or simultaneously. It should also be understood that these operations do not have to be performed all at once. At Step 510, operation of the motor 122 of the implantable blood pump 101 stops, e.g., due to a detected undesirable condition. At Step 520, the pump restart module 246 of the control circuit 201 receives a first pump restart input indicating clearance of the undesirable condition in order to restart operation of the pump 101. The first pump restart input may be automatically generated in response to clearance of the undesirable condition, or may be manually provided, directly or indirectly, by the patient or a clinician. At Step 524, the control circuit 201 determines whether the lockout mode (e.g., lockout state 330) has been activated by the pump restart lockout module 248. If the lockout mode has not been activated, then at Step 526, the control circuit 201 responds to the first pump restart input and restarts operation of the pump 101. However, if the lockout mode has been activated, then at 528, the control circuit 201 does not respond to the first pump restart input, instead preventing operation of the pump 101 from restarting. At Step 530, the pump restart module 246 of the control circuit 201 receives a second pump restart input (e.g., from the clinician) attempting to restart operation of the pump 101. At Step 532, the control circuit 201 restarts operation of the pump 101 in response to the second pump restart input. Even if the control circuit 201 is in lockout mode when the control circuit 201 receives the second pump restart input, the control circuit 201 nonetheless responds to the second pump restart input, and overrides the lockout mode. If the control circuit 201 was previously in lockout mode, that mode may also be reset at 536 in response to the second pump restart input.

In some cases, the second pump restart input may be an instruction to clear the lockout mode, which is interpreted by the control circuit 201 as an instruction to also restart the pump 101. In particular, where the first pump restart input is provided automatically, the instruction to clear the lockout mode may automatically result in the control circuit 201 responding to the pre-existing first pump restart input, which until clearance of the lockout mode was continuously overridden. In other cases, such as where the first pump restart input is manually entered, the second pump restart input may be a combination of an instruction to clear the lockout mode, followed by manual entry the first pump restart input. Ultimately, it should be understood that the first pump restart input and the second pump restart input do not necessarily constitute different ways of entering instructions to restart the pump, or different codes for restarting the pump. Rather, the difference between the first pump restart input and the second pump restart may be the presence of an instruction to clear the lockout mode and thus the second pump restart input is the same input as the first pump restart input with the addition of the instruction to clear the lockout mode.

In the above examples, the second pump restart input has been described as an input which the control circuit 201 cannot automatically execute, or which the patient cannot directly access, but rather must indirectly accessed by seeking assistance from a medical professional. However, it is also possible that the second pump restart input is technically accessible to the patient or clinician, but that the patient and clinician are simply trusted not to restart the pump 101 on without the patient first being examined when the pump 101 is in the lockout mode. In such a case, the lockout mode may simply prevent restarting of the pump 101 using a standard restart procedure (e.g., based on the above-described first pump restart input).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for controlling operation of an implantable blood pump having a motor with a control circuit, comprising:
   providing, from an interface in communication with the control circuit, one or more inputs to a pump control module to initiate a run state of the motor;
   providing, from the interface, one or more inputs to a pump shutdown module to cease operation of the motor;
   receiving, at a pump restart module from the interface, one from the group consisting of a first pump restart input and a second pump restart input configured to resume operation of the motor, the second pump restart input being different from the first pump restart input;
   measuring, at the control circuit, a duration of time in which operation of the motor has been stopped;
   comparing the measured duration of time in which operation of the motor has been stopped to a predetermined threshold;
   determining, at a pump restart module, whether the control circuit has initiated a pump lockout mode in response to a lockout input based on whether the measured duration of time in which operation of the motor has been stopped exceeds the predetermined threshold;
   in response to a determination that the pump lockout mode has not been initiated:
      resuming operation of the motor in response to one from the group consisting of the first pump restart input and the second pump restart input; and
   in response to a determination that the pump lockout mode has been initiated:
      resuming operation of the motor in response to the second pump restart input; and
      maintaining cessation of operation of the motor in response to the first pump restart input.

2. The method of claim 1, further comprising initiating the pump lockout mode at a predetermined amount of time after ceasing operation of the motor.

3. The method of claim 2, wherein the predetermined amount of time is based on a predicted risk of thrombosis in the implantable blood pump.

4. The method of claim 3, wherein the second pump restart input resets the predetermined amount of time.

5. The method of claim 1, wherein the second pump restart input is a manual input.

6. The method of claim 1, wherein the second restart pump input is inaccessible to a user of the implantable blood pump.

7. The method of claim 1, further comprising, in response to a determination that the pump lockout mode has been initiated, clearing the pump lockout mode in response to the second pump restart input.

8. The method of claim 1, further comprising notifying at least one of a user and a clinician of the implantable blood pump initiation of the pump lockout mode.

* * * * *